United States Patent [19]
Humke

[11] Patent Number: 6,071,931
[45] Date of Patent: Jun. 6, 2000

[54] AT$_1$-RECEPTOR ANTAGONISTS FOR PREVENTING AND TREATING POSTISCHEMIC RENAL FAILURE AND FOR PROTECTING ISCHEMIC KIDNEYS

[75] Inventor: Ulrich Humke, Homburg, Germany

[73] Assignee: Novartis AG, Basel, Switzerland

[21] Appl. No.: 09/051,345

[22] PCT Filed: Sep. 24, 1996

[86] PCT No.: PCT/EP96/04162

§ 371 Date: Apr. 6, 1998

§ 102(e) Date: Apr. 6, 1998

[87] PCT Pub. No.: WO97/13513

PCT Pub. Date: Apr. 17, 1997

[30] Foreign Application Priority Data

Oct. 6, 1995 [CH] Switzerland .............................. 2825/95

[51] Int. Cl.$^7$ .......................... A61K 31/44; A61K 31/41; A61K 31/415
[52] U.S. Cl. .......................... 514/303; 514/381; 514/394; 514/397
[58] Field of Search .................................... 514/303, 381, 514/394, 397

[56] References Cited

FOREIGN PATENT DOCUMENTS 0629408 12/1994 European Pat. Off. .
9405289 3/1994 WIPO .

OTHER PUBLICATIONS

Takishita et al., Hypertension, vol. 24, No. 4, 1994, pp. 445–450.
Huland et al., Urol Int, vol. 36, No. 1, 1981, pp. 15–22.
Huland et al., Transplantation, vol. 36, No. 2, 1983, pp. 139–142.
Dalaney et al., Anesthesiology, vol. 51, No. 3, 1979, p. s73.

*Primary Examiner*—Kimberly Jordan
*Attorney, Agent, or Firm*—Gregory D. Ferraro

[57] ABSTRACT

The compound (S)-N-(1-carboxy-2-methylprop-1-yl)-N-pentanoyl-N-[2'(1H-tetrazol-5-yl)biphenyl-4-yl-methyl]amine (valsartan) of formula

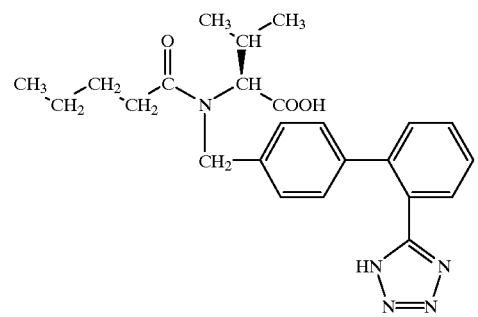

or a salt thereof, in particular a pharmaceutically acceptable salt thereof, can be used for treating (acute and chronic) postischemic renal failure and for protecting the ischemic kidney.

4 Claims, No Drawings

$AT_1$-RECEPTOR ANTAGONISTS FOR PREVENTING AND TREATING POSTISCHEMIC RENAL FAILURE AND FOR PROTECTING ISCHEMIC KIDNEYS

This application is a 371 of PCT/EP96/04162, filed Sep. 24, 1996.

The enzyme cascade of the renin-angiotensin system (RAS) comprises a series of bio chemical sequences and, as is known, there are different approaches for opening up possibilities for the treatment of, for example, hypertension by regulatory intervention.

Angiotensinogen, α2-macroglycoprotein, is split by the renin enzyme into the deca peptide angiotensin I, which itself is biologically only very weakly active. The next step in the cascade is the removal of a further two amino acids by the action of the angiotensin-converting enzyme (ACE), bonded mainly in the endothelium, with formation of angiotensin II. This latter is held to be one of the strongest natural vasoconstrictors.

The vasoconstrictive effects of angiotensin II are produced by its action on the non-striated muscle cells, the stimulation of the formation of the adrenergenic hormones epinephrine and norepinephrine as well as by the increase of the activity of the sympathetic nervous system as a result of the formation of norepinephrine. Angi otensin II also has an influence on the electrolytic balance, produces e.g. antinatriuretic and anitdiurectic effects in the kidney and accordingly promotes the release of, on the one hand, the vasopressin peptide from the pituitary gland and, on the other hand, of aldosterone from the adrenal glomerulosa. These influences all play an important part in the regulation of blood pressure.

Angiotensin II interacts with specific receptors on the surface of the target cell. It has been possible to identify receptor subtypes which are termed e.g. $AT_1$- and $AT_2$-receptors. Great efforts have been made lately to identify substances that bind to $AT_1$-receptors. Such active ingredients are often termed angiotensin II antagonists. Because of the inhibition of the $AT_1$-receptor such antagonists can be used e.g. as antihypertensives or for the treatment of congestive heart failure.

Angiotensin II antagonists are understood to mean those active ingredients which bind to the $AT_1$-receptor subtype. These include compounds having different structural features. Compounds to be mentioned are, for example, those cited in the compound claims of EP-443983, the subject matter of which is herewith incorporated by reference in this application.

A compound to be highlighted is (S)-N-(1-carboxy-2-methyl-prop-1-yl)-N-pentanoyl-N-[2'(1H-tetrazol-5-yl) biphenyl-4-yl-methyl]amine (hereinafter termed valsartan) of formula

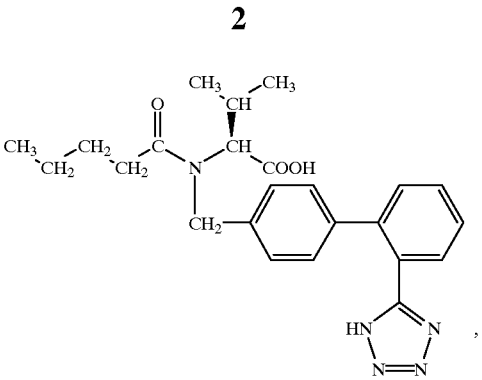

cited in European patent application having the publication no. EP-443983, Example 16, or a salt thereof, preferably a pharmaceutically acceptable salt thereof.

Furthermore, the compounds cited in the compound claims of European patent application having the publication no. EP-253310 are incorporated by reference in this application.

A compound to be highlighted is that of the following formula

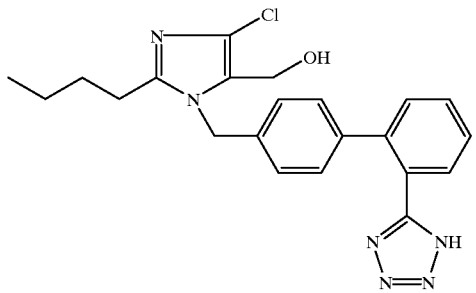

and the pharmaceutically acceptable salts thereof.

Furthermore, the compounds cited in the compound claims of European patent application having the publication no. EP-403159 are incorporated by reference in this application.

A compound to be highlighted is that of the following formula

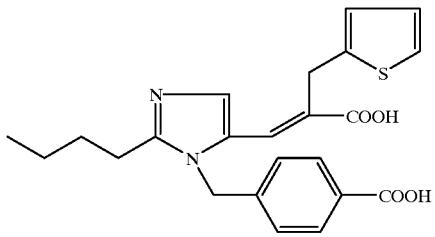

and the pharmaceutically acceptable salts thereof.

Furthermore, the compounds cited in the compound claims of PCT patent application WO 91/14679 are, with reference to this literature, herewith also included in this application.

A compound to be highlighted is that of the following formula

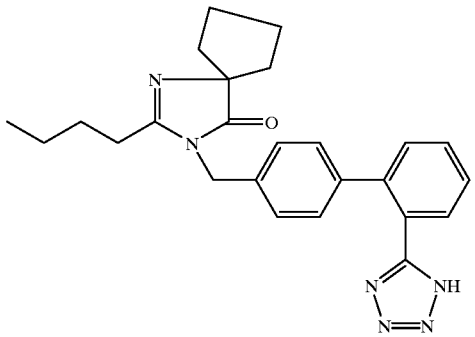

and the pharmaceutically acceptable salts thereof.

Furthermore, the compounds cited in the compound claims of European patent application having the publication no. EP-420 237 are incorporated by reference in this application.

A compound to be highlighted is that of the following formula

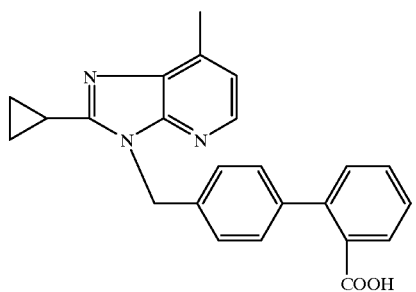

and the pharmaceutically acceptable salts thereof.

Furthermore, the compounds cited in the compound claims of European patent application having the publication no. EP-502314 are incorporated by reference in this application.

A compound to be highlighted is that of the following formula

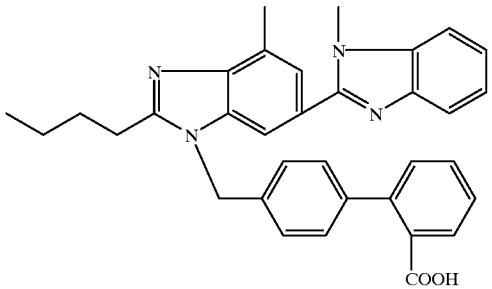

and the pharmaceutically acceptable salts thereof.

Furthermore, the compounds cited in the compound claims of European patent application having the publication no. EP-459136 are incorporated by reference in this application.

A compound to be highlighted is that of the following formula

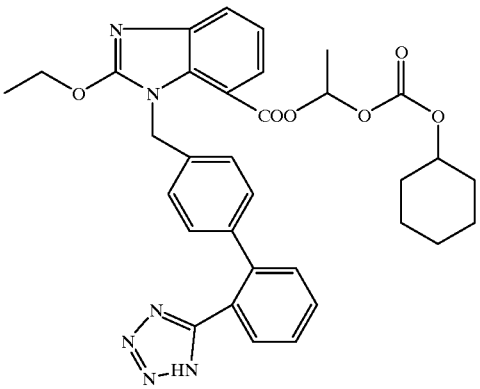

and the pharmaceutically acceptable salts thereof.

Furthermore, the compounds cited in the compound claims of European patent application having the publication no. EP-504888 are incorporated by reference in this application.

A compound to be highlighted is that of the following formula

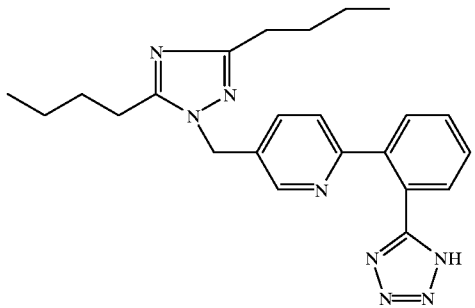

and the pharmaceutically acceptable salts thereof.

Furthermore, the compounds cited in the compound claims of European patent application having the publication no. EP-514198 are incorporated by reference in this application.

A compound to be highlighted is that of the following formula

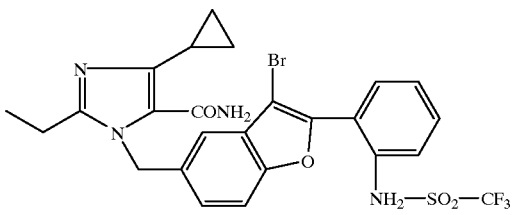

and the pharmaceutically acceptable salts thereof.

Furthermore, the compounds cited in the compound claims of European patent application having the publication no. EP-475206 are incorporated by reference in this application.

A compound to be highlighted is that of the following formula

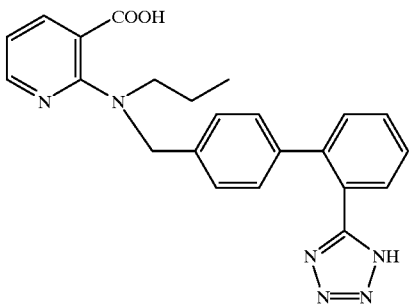

and the pharmaceutically acceptable salts thereof.

Furthermore, the compounds cited in the compound claims of PCT patent application WO 93/20816 are incorporated by reference included in this application.

A compound to be highlighted is that of the following formula

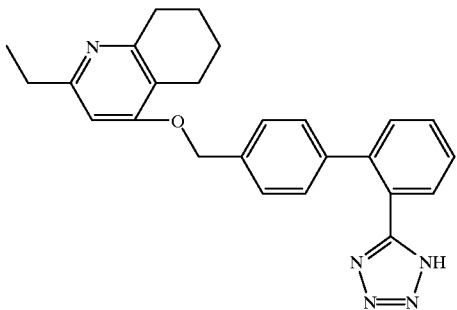

and the pharmaceutically acceptable salts thereof.

Pharmaceutically acceptable salts of valsartan, for example, are typically acid addition salts. These acid addition salts are formed, for example, with strong inorganic acids, typically mineral acids, such as sulfuric acid, a phosphoric acid or a hydrohalic acid, with strong organic carboxylic acids, typically with $C_1$–$C_4$ alkanecarboxylic acids which may be substituted, e.g. by halogen, typically acetic acid, for example with dicarboxylic acids which may be unsaturated, such as oxalic acid, malonic acid, succinic acid, maleic acid, fumaric acid, phthalic acid or terephthalic acid, for example with hydroxycarboxylic acids, such as ascorbic acid, glycolic acid, lactic acid, malic acid, tartaric acid or citric acid, for example with amino acids, such as aspartic acid or glutaminic acid, or e.g. benzoic acid, or with organic sulfonic acids, for example with $C_1$–$C_4$ alkanesulfonic acids or arylsulfonic acids which may be substituted, e.g. by halogen, for example with methane- or p-toluenesulfonic acid. Suitable salts with bases are typically metal salts, such as alkali metal salts or alkaline earth metal salts, typically sodium, potassium or magnesium salts, or salts with ammonia or an organic amine, such as morpholine, thiomorpholine, piperidine, pyrrolidine, a mono-, di- or tri-lower alkylamine, typically ethylamine, tert-butylamine, diethylamine, diisopropylamine, triethylamine, tributylamine or dimethylpropylamine, or a mono-, di- or trihydroxy-lower alkylamine, typically mono-, di- or triethanolamine. Corresponding internal salts can also be used.

In the case of acute renal failure, the rapid decline of the renal function leads to a retention of substances which are usually eliminated with the urine. The most common form of acute renal failure is the prerenal failure. This involves renal ischemia, which can be caused, for example, by haemorrhagic shock, intraoperative hypotonia or operatively induced disruption of renal blood flow (e.g. intentionally, by clamping the renal blood vessels, or unintentionally, by spasms of the vessels when the kidney is manipulated). If the renal ischemia lasts only a short time, the renal function can normalise quickly upon restoration of the renal perfusion. After prolonged renal ischemia, however, an acute tubular necrosis can often occur in spite of the kidney blood flow being restored, which in turn can lead to an acute renal failure with the known consequences. The interruption of the blood flow and hence of the oxygen supply results in a destabilisation of the cell membranes and finally in the passive equilibration of the intra- and extracellular gradients for the electrolyte concentrations. In addition to this direct damage to the individual cell, which is further aggravated by a rapidly increasing acidosis, vasoconstrictive substances are released which can lead to an increase in resistance of the peripheral intrarenal vascular system. Angiotensin II is one of these substances, which is therefore involved in preventing an immediate complete postischemic restoration of the blood flow of the organ. The prophylaxis and treatment of such postischemic renal failure is very important in order to achieve a normal renal function, especially after prolonged renal ischemia.

Accordingly, there is a considerable interest in the provision of a broad spectrum of different active ingredients which offer protection against postischemic renal failure. Particular emphasis is placed on such active ingredients which guarantee that, on the one hand, the least possible lowering of blood pressure for maintainance of the reperfusion pressure is obtained and, on the other hand, an increased renal blood flow (RBF) effect is produced. A low renal vascular resistance (RVR) causes an increase in the RBF. The RVR factor can be expressed as quotient of the medium arterial blood pressure (MAP) and the renal blood flow (RBF). In a normal functioning kidney the RVR factor is low.

It is known that active ingredients with an endothelin-antagonising profile can be used for treating postischemic renal failure. Specific $AT_1$-receptor antagonists, however, have so far not been known to have such effects.

Surprisingly, it has now been found that, while lowering the blood pressure only little, $AT_1$-receptor antagonists increase the RBF because they keep the RVR low, and accordingly they also have a substantial profile for treating postischemic renal failure and for protecting the ischemic kidney.

The protective effect of $AT_1$-receptor antagonists on the ischemic kidney, e.g. by the use of valsartan, can be manifested, for example, by the following experimental procedure:

Vascular catheters are introduced under halothane inhalation anaesthesia into the arteria carotis communis and the vena jugularis externa of male Sprague-Dawley rats weighing 200 to 250 g and a silicone catheter with two lumina is implanted into their bladder. All catheters are inserted subcutaneously, exiting at a small incision in the skin of the neck and fixed there, out of reach of the animal.

Intravenous injection of either a control substance (NaCl 0.9%, 1 ml/kg) or of the $AT_1$-receptor antagonist, e.g. in the case of valsartan (0.3 mg/kg), is then carried out in two test groups. 30 minutes after the injection, the left kidney is exposed via an incision in the flank and the complete vascular pedicle is clamped for 60 minutes with a vascular clamp. During this induced ischemia the animal is kept under a shallow anaesthesia. With continuous rectal measurement of the temperature, the body temperature is adjusted to a constant 37.8° C. via a control system with external red light irradiation. After 60 minutes of ischemia the clamp is removed and the contralateral intact kidney is exstipated via an incision on the other flank.

The animals are then divided into 2 groups.

Group 1: acute test (measurement of the renal function up to 3 hours after the ischemia)

Group 2: chronic test (measurement of the renal function 48 hours after the ischemia).

Group 1: After waking from their anaesthesia, the animals are positioned in a rest cage. Intravenous saturation and long-term administration of the clearance markers inulin and paraaminohippuric acid is then carried out with the object of equilibration. The urine is constantly suctioned off via a pump and 90, 120 and 150 minutes after the ischemia the renal function is measured via the clearance of the indicated marker substances with three 30-minute collecting periods and corresponding blood samplings as well as simultaneous intra-arterial measurement of the blood pressure. The animal is stress-free and conscious during all of this. After the test the ischemically damaged kidney is removed.

Group 2: After ischemia and nephrectomy, the animal is transferred into its cage for 48 hours. After 48 hours the renal function is measured via 3 measuring periods as described for group 1.

The collected urine samples are gravimetrically determined. The concentration of the clearance markers inulin and paraaminohippuric acid in the urine and plasma are photometrically determined with conventional biochemical methods. Electrolytes and creatinine in urine and plasma are determined using a multianalyser. The haematocrit determination is carried out separately for each measuring period. While urine output, arterial blood pressure, glomerulary filtration rate and renal plasma flow are directly measured, the filtration fractions, renal blood flow and renal vascular resistance are calculated from the corresponding measured values. Normal or starting values, with which postischemic values are compared, are determined from prior test groups with rats of the same weight which serve as measurements of the physiological changes of the test substances in intact kidneys.

The evaluation of the pharmacological experiments of the animals of control group 1 shows a low glomerular filtration rate (8% as compared to non-ischemic values) as well as a low renal blood flow (3% as compared to non-ischemic values). In contrast thereto, a markedly enhanced glomerular filtration rate (22% as compared to non-ischemic values) as well as a significantly increased blood flow (23% as compared to non-ischemic values) could be observed for the rats of group 2 which were treated with e.g. valsartan. The high renal vascular resistance (RVR) could be reduced by 95% in group 2.

Accordingly, $AT_1$-receptor antagonists can be used for treating (acute and chronic) postischemic renal failure and for protecting the ischemic kidney.

$AT_1$-Receptor antagonists can be used in particular before and after operations of the vascular system or of the aorta, for example after major heart operations, in the case of intended ischemia of the kidney by clamping the renal vascular pedicle (e.g. in the case of hypoperfusions of the kidney during corresponding operations, renal tumour operations, renal artery operations, kidney stone operations, kidney transplantations) or can be preventively administered to the donor in kidney transplantations. Nephrotoxic problems, extracellular volume depletions, cardiac or renal failure induced by moderate renal perfusion as well as the Crush Syndrome can also be treated.

It is the object of this invention to provide pharmaceutical compositions for preventing and treating postischemic renal failure and for protecting the ischemic kidney, which composition comprises an $AT_1$-receptor antagonist, in particular valsartan, or a pharmaceutically acceptable salt thereof.

The invention also relates to the use of an $AT_1$-receptor antagonist, in particular valsartan, or of a pharmaceutical salt thereof for the preparation of a pharmaceutical composition for preventing and treating postischemic renal failure and for protecting the ischemic kidney by administering a therapeutically effective amount of valsartan or of a pharmaceutically acceptable salt thereof.

The invention also relates to a process for preventing and treating postischemic renal failure and for protecting the ischemic kidney, which process comprises administering a therapeutically effective amount of valsartan or of a pharmaceutical salt thereof.

The invention also relates to the use of an $AT_1$-receptor antagonist or of a pharmaceutical salt thereof for preventing and treating postischemic renal failure and for protecting the ischemic kidney.

Said pharmaceutical compositions are those for enteral, such as oral, and also rectal or parenteral administration to warm-blooded animals, the pharmacological active ingredient being present on its own or together with the usual pharmaceutical excipients. The pharmaceutical compositions contain, for example, from about 0.1% to 100%, preferably from about 1% to about 80%, of the active ingredient. Pharmaceutical compositions for enteral or parenteral and also for ocular administration are typically those in unit dose forms, such as dragées, tablets, capsules or suppositories and also ampoules. These are prepared in a manner known per se, for example by means of conventional mixing, granulating, sugar-coating, dissolving or lyophilising methods. Accordingly, pharmaceutical compositions for oral use can be obtained by combining the active ingredient with solid carriers, if desired granulating a mixture obtained, and processing the mixture or granules, if desired or necessary after the addition of suitable excipients, to give tablets or dragée cores.

Suitable carriers are preferably fillers, typically sugars, such as lactose, saccharose, mannitol or sorbitol, cellulose compositions and/or calcium phosphates, e.g. tricalcium phosphate or calciumhydrogen phosphate, furthermore binders, such as starch paste, typically using e.g. corn starch, wheat starch, rice starch or potato starch, gelatin, tragacanth gum, methylcellulose and/or polyvinylpyrrolidone and, if desired, disintegrants, such as the above-mentioned starches, furthermore carboxymethyl starch, crosslinked polyvinylpyrrolidone, agar, alginic acid or a salt thereof, typically sodium alginate. Excipients are primarily flow regulators and lubricants, typically silica gel, talcum, stearic acid or salts thereof, typically magnesium stearate or calcium stearate, and/or polyethylene glycol. Dragée cores are provided with suitable coatings which, if desired, are resistant to gastric juice, using, inter alia, concentrated sugar solutions which optionally contain gum arabic, talcum, polyvinylpyrrolidone, polyethylene glycol and/or titanium dioxide, coating solutions in suitable organic solvents or solvent mixtures or, for the preparation of gastric juice-resistant coatings, solutions of suitable cellulose compositions, typically acetylcellulose phthalate or hydroxypropylmethylcellulose phthalate. Colourants or pigments may be added to the tablets or dragée coatings, for example to identify or indicate different doses of active ingredient.

Other pharmaceutical compositions for oral administration are dry-filled gelatin capsules as well as soft closed capsules made of gelatin and a plasticiser, such as glycerol or sorbitol. The dry-filled capsules may contain the active ingredient in the form of granules, typically in admixture with fillers, such as lactose, binders, such as starches, and/or lubricants, such as talcum or magnesium stearate. In soft capsules, the active ingredient is preferably dissolved or suspended in suitable liquids, such as fatty oils, paraffin oil or liquid polyethylene glycols, and stabilisers can also be added.

Suitable pharmaceutical compositions for rectal administration are typically suppositories consisting of a combination of the active ingredient with a suppository base. Suitable suppository bases are, for example, natural or synthetic triglycerides, paraffin hydrocarbons and higher alkanols. Furthermore, gelatin rectal capsules containing a combination of the active ingredient with a base substance may also be used. Suitable base substances are, for example, liquid triglycerides, polyethylene glycols or paraffin hydrocarbons.

Suitable compositions for parenteral administration are primarily aqueous solutions of an active ingredient in water-soluble form, typically a water-soluble salt, and also suspensions of the active ingredient, such as appropriate oily injection suspensions, using suitable lipophilic solvents or vehicles, typically fatty oils, e.g. sesame oil, or synthetic fatty acid esters, typically ethyl oleate or triglycerides, or aqueous injection suspensions containing viscosity-increasing substances, e.g. sodium carboxymethylcellulose, sorbitol and/or dextran and, optionally, also stabilisers.

For preventive treatments, unit dosage forms for oral administration are preferred, typically tablets or capsules and, in acute treatments, i.v. application forms.

The dose of the active ingredient can depend of various factors, e.g. mode of application, species of warm-blooded animal, age and/or individual state. The estimated normal dose for oral administration to a patient weighing about 75 kg is an approximate dose of about 10 mg to about 250 mg of $AT_1$-receptor antagonist.

In a preferred embodiment of this invention, pharmaceutically acceptable compositions comprising valsartan are used. The daily dose for oral administration of $AT_1$-antagonist valsartan in a unit dose form is preferably about 20 mg to about 160 mg, more preferably about 40 mg or about 80 mg.

The following Example illustrates the above invention without, however, limiting it in its scope in any way.

Formulation Example 1

A hard gelatin capsule, comprising as active ingredient e.g. (S)-N-(1-carboxy-2-methyl prop-1-yl)-N-pentanoyl-N-[2'(1H-tetrazol-5-yl)biphenyl-4-yl-methyl]amine, can be formulated, for example, as follows:

| Composition: | |
|---|---|
| (1) valsartan | 80.0 mg |
| (2) microcrystalline cellulose | 110.0 mg |
| (3) polyvidone K30 | 45.2 mg |
| (4) sodium lauryl sulfate | 1.2 mg |
| (5) crospovidone | 26.0 mg |
| (6) magnesium stearate | 2.6 mg |

Components (1) and (2) are granulated with a solution of components (3) and (4) in water. The components (5) and (6) are added to the dry granulate and the mixture is filled into size 1 hard gelatin capsules.

What is claimed is:

1. A method for treating chronic postischemic renal failure in a mammal that has previously undergone a trauma or an operation where ischemia of the kidney has occurred which comprises administering to a mammal that has previously undergone a trauma or an operation where ischemia of the kidney has occurred a therapeutically effective amount for treating chronic postischemic renal failure of an AT1-receptor antagonist or of a pharmaceutical salt thereof.

2. A method according to claim 1 wherein the trauma or operation is selected from a operation of the vascular system which causes hypoperfusion of the kidney, an operation which requires clamping the vascular pedicle, an operation to remove a renal tumor, an operation on a renal artery, an operation to remove a kidney stone, a kidney transplantation operation, a nephrotoxicity problem, an extracellular volume depletion, cardiac or renal failure induced by moderate renal perfusion, and the Crush Syndrome.

3. A method according to claim 1 wherein the $AT_1$-receptor antagonist is selected from the group consisting of:

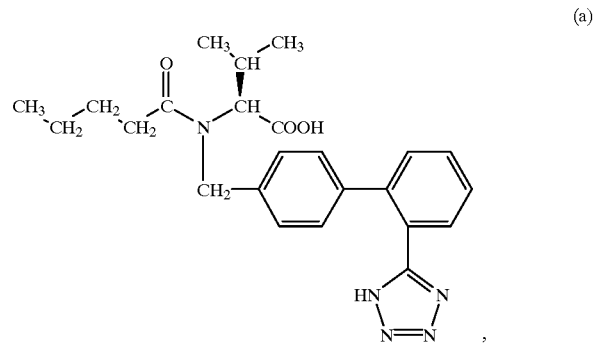

(a)

-continued
(b)
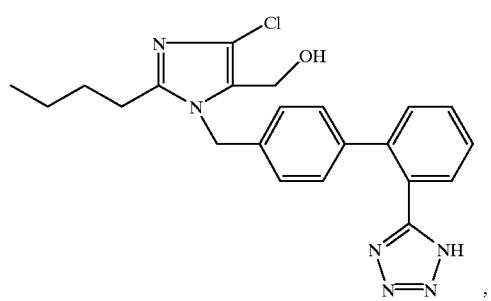
(c)
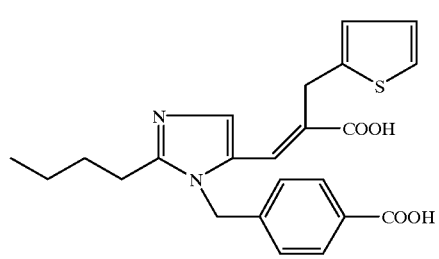
(d)
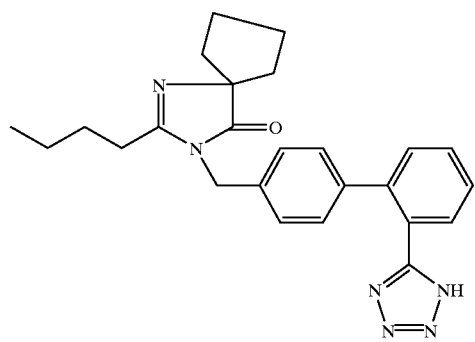
(e)
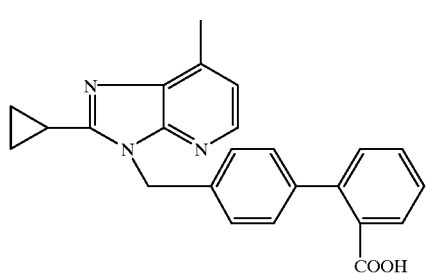
(f)
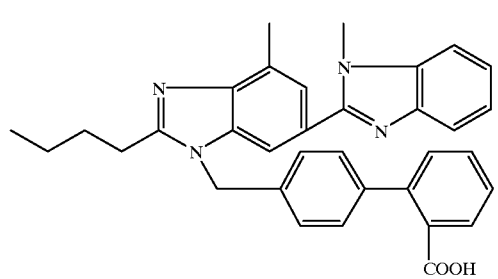

(g)
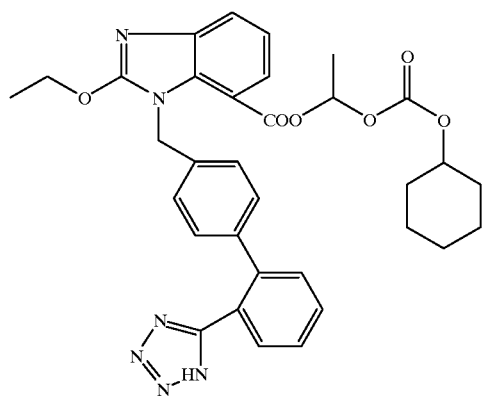
(h)
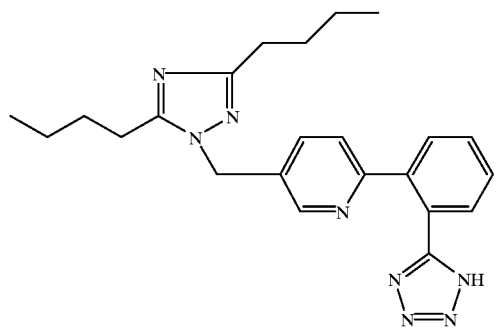
(i)
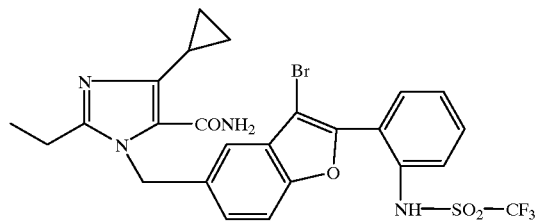
(j)
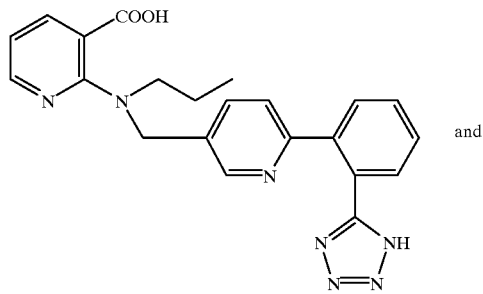 and

-continued
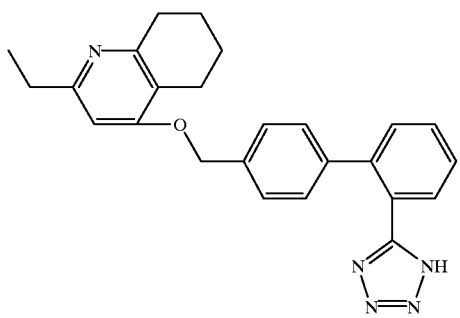
(k)
or, in each case, a pharmaceutically acceptable salt thereof.
4. A method according to claim 1 wherein the AT$_1$-receptor antagonist is valsartan of formula
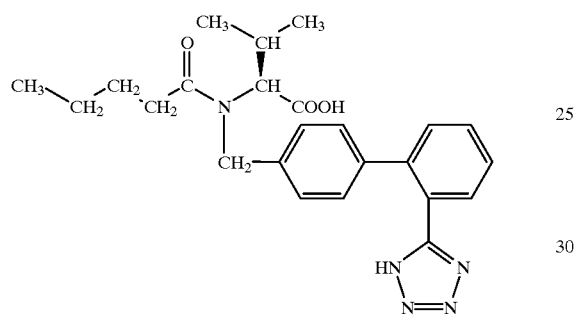
or a pharmaceutically acceptable salt thereof.
* * * * *